(12) United States Patent
Pazenok et al.

(10) Patent No.: US 9,701,640 B2
(45) Date of Patent: Jul. 11, 2017

(54) PROCESS FOR PREPARING 3,5-BIS(HALOALKYL)PYRAZOLE DERIVATIVES FROM α,α-DIHALOAMINES AND KETIMINES

(71) Applicant: BAYER CROPSCIENCE AKTIENGESELLSCHAFT, Monheim am Rhein (DE)

(72) Inventors: Sergii Pazenok, Solingen (DE); Norbert Lui, Odenthal (DE); Christian Funke, Leichlingen (DE); Winfried Etzel, Leichlingen (DE); Arnd Neeff, Burscheid (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/127,908

(22) PCT Filed: Mar. 20, 2015

(86) PCT No.: PCT/EP2015/055899
§ 371 (c)(1),
(2) Date: Sep. 21, 2016

(87) PCT Pub. No.: WO2015/144578
PCT Pub. Date: Oct. 1, 2015

(65) Prior Publication Data
US 2017/0088521 A1    Mar. 30, 2017

(30) Foreign Application Priority Data

Mar. 24, 2014  (EP) .................................... 14161337
Nov. 3, 2014   (EP) .................................... 14191501

(51) Int. Cl.
C07D 231/12   (2006.01)
C07C 251/08   (2006.01)
C07F 5/02     (2006.01)
C07D 231/14   (2006.01)

(52) U.S. Cl.
CPC .......... *C07D 231/12* (2013.01); *C07C 251/08* (2013.01); *C07D 231/14* (2013.01); *C07F 5/022* (2013.01)

(58) Field of Classification Search
None
See application file for complete search history.

(56) References Cited

U.S. PATENT DOCUMENTS

| 7,358,387 | B2 | 4/2008  | Lantzsch et al. |
| 7,939,673 | B2 | 5/2011  | Pazenok et al.  |
| 8,350,053 | B2 | 1/2013  | Pazenok et al.  |
| 8,436,191 | B2 | 5/2013  | Pazenok et al.  |
| 8,592,605 | B2 | 11/2013 | Pazenok et al.  |
| 8,629,288 | B2 | 1/2014  | Pazenok et al.  |
| 8,765,971 | B2 | 7/2014  | Pazenok et al.  |
| 9,096,535 | B2 | 8/2015  | Pazenok et al.  |
| 9,309,202 | B2 | 4/2016  | Pazenok et al.  |
| 2016/0185731 | A1 | 6/2016 | Pazenok et al. |

FOREIGN PATENT DOCUMENTS

| EP | 2325173 A1 | 5/2011 |
| EP | 2623496 A1 | 8/2013 |
| EP | 2628722 A1 | 8/2013 |
| WO | 2005042468 A1 | 5/2005 |
| WO | 2008022777 A2 | 2/2008 |
| WO | 2009106230 A2 | 9/2009 |
| WO | 2009112157 A1 | 9/2009 |
| WO | 2012137982 A2 | 10/2012 |
| WO | 201313829 A1 | 8/2013 |
| WO | 2013135824 A2 | 9/2013 |
| WO | 2013142307 A1 | 9/2013 |
| WO | 2014124878 A1 | 8/2014 |

OTHER PUBLICATIONS

International Search Report dated Apr. 20, 2015, issued in PCT/EP2015/055899.
Gerus et al., 'Reported, but Still Unknown' A Closer Look into 3,4-Bis-and 3,4,5-Tris(trifluoromethyl)pyrazoles. The Journal of Organic Chemistry. (2012) vol. 77: 47-56.
Preet et al., "3,5-Bis(Trifluoromethyl) Pyrazole and Some N-Substituted Derviatives" Journal of Fluorine Chemistry. (1991). vol. 51: 283-289.
Sloop et al., "Synthesis of fluorinated heterocycles" Journal of Fluorine Chemistry. (2002). pp. 135-147.
Pruitt et al., Discovery of 1-(2-Aminomethylphenyl)-3-trifluoromethyl-N-[3-fluoro-2'-(aminosulfonyl) [1,1'piphenyl)]-1H-pyrazole-5-carboxyamide(DPC602), a Potent, Selective, and Orally Bioavailable Factor Xa Inhibitor. J. Med. Chem. (2003) vol. 46: 5298-5315.
Pashkevich et al., XP009179740 (1981) pp. 105-107.
Yu et al., "A convenient synthesis of 3-polyfluoroalkyl pyrazoles and 6-polyfluoroalkyl pyrimidines from B-polyfluoroalkyl enaminones" Journal of Fluorine Chemistry. (1997). vol. 84: 65-67.

*Primary Examiner* — Kamal Saeed
(74) *Attorney, Agent, or Firm* — McBee Moore Woodward Vanik LLC; Susan McBee; David Woodward

(57) ABSTRACT

The present invention relates to a novel process for preparing 3,5-bis(haloalkyl)pyrazole derivatives from α,α-dihaloamines and ketimines.

9 Claims, No Drawings

PROCESS FOR PREPARING 3,5-BIS(HALOALKYL)PYRAZOLE DERIVATIVES FROM α,α-DIHALOAMINES AND KETIMINES

CROSS REFERENCE TO RELATED APPLICATIONS

This application is a §371 National Stage Application of PCT/EP2015/055899 filed Mar. 20, 2015, which claims priority to EP 14161337.2, filed Mar. 24, 2014 and EP 14191501.7 filed Nov. 3, 2014.

BACKGROUND

Field of the Invention

The present invention relates to a novel process for preparing 3,5-bis(haloalkyl)pyrazole derivatives from α,α-dihaloamines and ketimines.

Description of Related Art

Polyfluoroalkylpyrazolylcarboxylic acid derivatives and 3,5-bis(haloalkyl)pyrazoles are valuable precursors of active fungicidal ingredients (WO 2003/070705, WO 2008/013925, WO 2012/025557).

Pyrazolecarboxylic acid derivatives are typically prepared by reacting acrylic acid derivatives having two leaving groups with hydrazines (WO 2009/112157 and WO 2009/106230). WO 2005/042468 discloses a process for preparing 2-dihaloacyl-3-aminoacrylic esters by reacting acid halides with dialkylaminoacrylic esters and subsequent cyclization thereof with alkyl hydrazines. WO 2008/022777 describes a process for preparing 3-dihalomethylpyrazole-4-carboxylic acid derivatives by reacting α,α-difluoroamines in the presence of Lewis acids with acrylic acid derivatives and subsequent reaction thereof with alkylhydrazines.

3,5-bis(fluoroalkyl)pyrazoles are prepared by reacting bisperfluoroalkyl diketones (e.g. 1,1,1,5,5,5-hexafluoroacetylacetone) with hydrazines (cf. Pashkevich et al., Zhurnal Vsesoyuznogo Khimicheskogo Obshchestva im. D. I. Mendeleeva (1981), 26(1), 105-7, the yield being only 27-40%. The synthesis, isolation and purification of the polyfluoroalkyl diketones is very complex since the compounds are generally very volatile and highly toxic.

SUMMARY

In the light of the prior art described above, it is an object of the present invention to provide a process that does not have the aforementioned disadvantages and hence gives a route to 3,5-bis(haloalkyl)pyrazole derivatives in high yields.

The object described above was achieved by a process for preparing 3,5-bis(haloalkyl)pyrazoles of the formula (Ia) and (Ib),

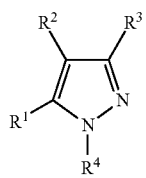

(Ia)

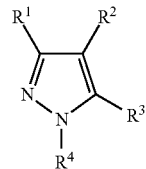

(Ib)

in which
$R^1$ and $R^3$ are each independently selected from $C_1$-$C_6$-haloalkyl;
$R^2$ is selected from H, halogen, COOH, (C=O)OR$^5$, CN and (C=O)NR$^6$R$^7$;
$R^4$ is selected from H, $C_1$-$C_5$-alkyl, $CH_2COOC_1$-$C_8$-alkyl, aryl, pyridyl;
$R^5$ is selected from $C_1$-$C_{12}$-alkyl, $C_3$-$C_8$-cycloalkyl, $C_6$-$C_{18}$-aryl, $C_7$-$C_{19}$-arylalkyl and $C_7$-$C_{19}$-alkylaryl;
$R^6$ and $R^7$ are each independently selected from $C_1$-$C_{12}$-alkyl, $C_3$-$C_8$-cycloalkyl, $C_7$-$C_{19}$-arylalkyl and $C_7$-$C_{19}$-alkylaryl or where
$R^6$ and $R^7$ together with the nitrogen atom to which they are bonded may form a four-, five- or six-membered ring characterized in that in step (A), α,α-dihaloamines of the formula (II),

(II)

in which
$R^1$ is as defined above;
X is independently selected from F, Cl or Br,
$R^{10}$ and a $R^{11}$ are each independently selected from $C_1$-$C_{12}$-alkyl, $C_3$-$C_8$-cycloalkyl, $C_7$-$C_{19}$-arylalkyl and $C_7$-$C_{19}$-alkylaryl or where
$R^{10}$ and $R^{11}$ together with the nitrogen atom to which they are bonded may form a five- or six-membered ring;
are reacted with compounds of the formula (III),

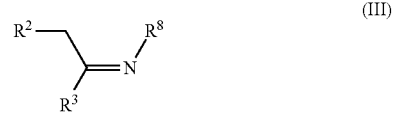

(III)

in which
$R^8$ is selected from $C_1$-$C_{12}$-alkyl, $C_3$-$C_8$-cycloalkyl, $C_6$-$C_{18}$-aryl, $C_7$-$C_{19}$-arylalkyl and $C_7$-$C_{19}$-alkylaryl, OR$^9$;
$R^9$ is selected from $C_1$-$C_{12}$-alkyl, $C_3$-$C_8$-cycloalkyl, $C_6$-$C_{18}$-aryl, $C_7$-$C_{19}$-arylalkyl, $C_7$-$C_{19}$-alkylaryl;
$R^2$ and $R^3$ are as defined above;
to form the compound of formula (V): (V-1), (V-2), (V-3), (V-4) and (V-5)

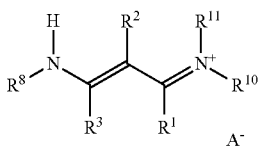

(V-1)

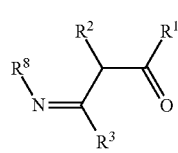

(V-2)

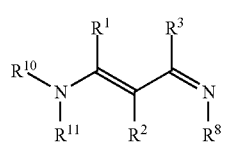

(V-3)

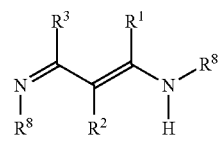

(V-4)

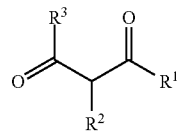

(V-5)

$A^-$ is $BF_4^-$, $AlCl_3F^-$, $AlF_2Cl_2^-$, $AlF_3Cl^-$ or $ZnCl_2F^-$ $R^1, R^2, R^3, R^5, R^6, R^7, R^8, R^9, R^{10}, R^{11}$ are as defined above and that in step (B) in the presence of hydrazine $H_2N-NHR^4$ (IV)—with $R^4$ being as defined above—a cyclization of (V) takes place to form (Ia/Ib).

Preferred is a process according to the invention, where the radicals in formula (Ia), (Ib), (II), (III), (IV) and (V) are defined as follows:

$R^1$ and $R^3$ are each independently selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl($CF_3CFH$), pentafluoroethyl and 1,1,1-trifluoroprop-2-yl;

$R^2$ is selected from H, F, Cl, Br, $COOCH_3$, $COOC_2H_5$, $COOC_3H_7$, CN and $CON(CH_3)_2$, $CON(C_2H_5)_2$;

$R^4$ is selected from H, $C_1$-$C_8$-alkyl, $CH_2COOC_1$-$C_8$-alkyl, phenyl, pyridyl;

$R^8$ are each independently selected from methyl, ethyl, n-, iso-propyl, n-, iso-, sec- and t-butyl, cyclopropyl, cyclobutyl, cyclopentyl, cyclohexyl, phenyl, benzyl, phenylethyl, $C_7$-$C_{19}$-alkylaryl, tolyl, 2,3-, 2,4-, 2,5-, 2,6-, 3,4- or 3,5-dimethylphenyl;

X is independently selected from F or Cl;

$R^{10}$ and $R^{11}$ are each independently selected from $C_1$-$C_{12}$-alkyl, $C_3$-$C_8$-cycloalkyl, $C_7$-$C_{19}$-arylalkyl or $R^{10}$ and $R^{11}$ together with the nitrogen atom to which they are bonded may form a five-membered ring.

DETAILED DESCRIPTION OF A PREFERRED EMBODIMENT

More preferred is a process according to the invention, where the radicals in formula (Ia), (Ib), (II), (III), (IV) and (V) are defined as follows:

$R^1$ and $R^3$ are each independently selected from trifluoromethyl, difluoromethyl, difluorochloromethyl, pentafluoroethyl;

$R^2$ is selected from H, Cl, CN, $COOC_2H_5$;

$R^4$ is selected from H, methyl, ethyl, n-, isopropyl, n-, iso-, sec- and t-butyl, n-pentyl, n-hexyl, 1,3-dimethylbutyl, 3,3-dimethylbutyl, phenyl, $CH_2COOCH_3$, $CH_2COOCH_2CH_3$;

$R^8$ is selected from methyl, ethyl, n-, iso-propyl, n-, iso-, sec- and t-butyl, cyclopropyl, cyclobutyl, cyclopentyl, cyclohexyl, benzyl, $C_7$-$C_{19}$-alkylaryl;

X is independently selected from F or Cl;

$R^{10}$ and $R^{11}$ are each independently selected from $C_1$-$C_{12}$-alkyl, $C_3$-$C_8$-cycloalkyl.

Even more preferred is a process according to the invention, where the radicals in formula (Ia), (Ib), (II), (III), (IV) and (V) are defined as follows:

$R^1$ and $R^3$ are each independently selected from $CF_2H$ and $CF_3$;

$R^2$ is selected from H or $COOC_2H_5$;

$R^4$ selected form H, methyl, ethyl, $CH_2COOCH_3$, $CH_2COOCH_2CH_3$, phenyl;

$R^8$ is selected from ethyl, n-, iso-propyl, n-, cyclopentyl, cyclohexyl, benzyl;

X is F;

$R^{10}$ and $R^{11}$ are each independently selected from $C_1$-$C_{12}$-alkyl.

Most preferred is a process according to the invention, where the radicals in formula (Ia), (Ib), (II), (III), (IV) and (V) are defined as follows:

$R^1$ and $R^3$ are $CF_2H$;

$R^2$ is H;

$R^4$ is selected from H, methyl, $CH_2COOCH_2CH_3$, phenyl;

$R^8$ is selected from iso-propyl and benzyl;

X is F;

$R^{10}$ and $R^{11}$ are each independently selected from methyl and ethyl.

Surprisingly, the pyrazoles of the formula (I) can be prepared under the inventive conditions with good yields and in high purity, which means that the process according to the invention overcomes the abovementioned disadvantages of the preparation processes previously described in the prior art.

A further aspect of the present invention are compounds of formula (III-a):

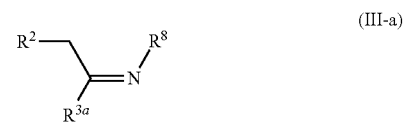

(III-a)

in which $R^{3a}$ is $HCF_2$;

$R^2$, $R^8$, $R^9$ are as defined above.

Preferred are compounds of formula (III-a) in which $R^{3a}$ is $HCF_2$;

$R^2$ is H;

$R^8$ is selected from $C_1$-$C_{12}$-alkyl, $C_3$-$C_8$-cycloalkyl, benzyl.

More preferred are compounds of formula (III-a) in which $R^{3a}$ is $HCF_2$;

$R^2$ is H;

$R^8$ is selected from iso-propyl, benzyl.

A further aspect of the present invention are compounds of formula (V-1):

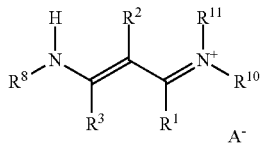

(V-1)

in which the radicals are as defined above.

Preferred are compounds of formula (V-1) in which
$R^1$ and $R^3$ are $HCF_2$;
$R^2$ is H;
$R^8$ is selected from $C_1$-$C_{12}$-alkyl, $C_3$-$C_8$-cycloalkyl and benzyl;
$R^{10}$ and $R^{11}$ are each independently selected from $C_1$-$C_5$ alkyl;
$A^-$ is $BF_4^-$.

More Preferred are compounds of formula (V-1) in which
$R^1$ and $R^3$ are $HCF_2$;
$R^2$ is H;
$R^8$ is selected from iso-propyl and benzyl;
$R^{10}$ and $R^{11}$ are each independently selected from methyl and ethyl;
$A^-$ is $BF_4^-$.

A further aspect of the present invention are compounds of formula (V-2):

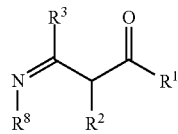

(V-2)

in which the radicals are as defined above.

Preferred are compounds of formula (V-2) in which
$R^1$ and $R^3$ are $HCF_2$;
$R^2$ is H;
$R^8$ is selected from $C_1$-$C_{12}$-alkyl, $C_3$-$C_8$-cycloalkyl and benzyl.

More preferred are compounds of formula (V-2) in which
$R^1$ and $R^3$ are $HCF_2$;
$R^2$ is H;
$R^8$ is selected from iso-propyl and benzyl.

A further aspect of the present invention are compounds of formula (V-3):

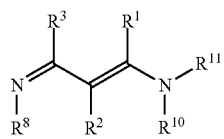

(V-3)

in which the radicals are as defined above.

Preferred are compounds of formula (V-3) in which
$R^1$ and $R^3$ are $HCF_2$;
$R^2$ is H;
$R^8$ is selected from $C_{1-12}$-alkyl, $C_{3-8}$-cycloalkyl and benzyl;
$R^{10}$ and $R^{11}$ are each independently selected from $C_{1-5}$ alkyl.

More preferred are compounds of formula (V-3) in which
$R^1$ and $R^3$ are $HCF_2$;
$R^2$ is H;
$R^8$ is selected from iso-propyl and benzyl;
$R^{10}$ and $R^{11}$ are each independently selected from methyl and ethyl.

A further aspect of the present invention are compounds of formula (V-4):

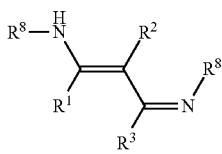

(V-4)

in which the radicals are as defined above.

Preferred are compounds of formula (V-4) in which
$R^1$ and $R^3$ are $HCF_2$;
$R^2$ is H;
$R^8$ is selected from $C_{1-12}$-alkyl, $C_{3-8}$-cycloalkyl and benzyl.

More preferred are compounds of formula (V-4) in which
$R^1$ and $R^3$ are $HCF_2$;
$R^2$ is H;
$R^8$ is selected from iso-propyl and benzyl.

A further aspect of the present invention are compounds of formula (V-5):

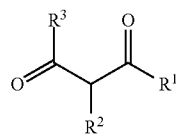

(V-5)

in which
$R^1$ and $R^3$ are each independently selected from $HCF_2$, $CF_3$, $CF_2Cl$;
$R^2$ is H.

GENERAL DEFINITIONS

In the context of the present invention, the term "halogen" (Hal), unless defined differently, comprises those elements which are selected from the group comprising fluorine, chlorine, bromine and iodine, preferably fluorine, chlorine and bromine, more preferably fluorine and chlorine.

Optionally substituted groups may be mono- or polysubstituted, where the substituents in the case of polysubstitutions may be the same or different.

Haloalkyl: straight-chain or branched alkyl groups having 1 to 6 and preferably 1 to 3 carbon atoms (as specified above), where some or all of the hydrogen atoms in these groups may be replaced by halogen atoms as specified above, for example (but not limited to) $C_1$-$C_3$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro, 2-difluoroethyl, 2,2-dichloro-2-fluoroethyl, 2,2,2-trichloroethyl, pentafluoroethyl and 1,1,1-trifluoroprop-2-yl. This definition also applies to haloalkyl as part of a composite substituent, for example haloalkylaminoalkyl etc., unless defined elsewhere. Preference is given to alkyl groups substituted by one or more halogen atoms, for example trifluoromethyl($CF_3$), difluoromethyl($CHF_2$), $CF_3CH_2$, $CF_2Cl$ or $CF_3CCl_2$.

Alkyl groups in the context of the present invention, unless defined differently, are linear, branched or cyclic saturated hydrocarbyl groups. The definition $C_1$-$C_{12}$-alkyl encompasses the widest range defined herein for an alkyl group. Specifically, this definition encompasses, for example, the meanings of methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl or n-dodecyl.

Alkenyl groups in the context of the present invention, unless defined differently, are linear, branched or cyclic hydrocarbyl groups containing at least one single unsaturation (double bond). The definition $C_2$-$C_{12}$-alkenyl encompasses the widest range defined herein for an alkenyl group. Specifically, this definition encompasses, for example, the meanings of vinyl; allyl(2-propenyl), isopropenyl(1-methylethenyl); but-1-enyl(crotyl), but-2-enyl, but-3-enyl; hex-1-enyl, hex-2-enyl, hex-3-enyl, hex-4-enyl, hex-5-enyl; hept-1-enyl, hept-2-enyl, hept-3-enyl, hept-4-enyl, hept-5-enyl, hept-6-enyl; oct-1-enyl, oct-2-enyl, oct-3-enyl, oct-4-enyl, oct-5-enyl, oct-6-enyl, oct-7-enyl; non-1-enyl, non-2-enyl, non-3-enyl, non-4-enyl, non-5-enyl, non-6-enyl, non-7-enyl, non-8-enyl; dec-1-enyl, dec-2-enyl, dec-3-enyl, dec-4-enyl, dec-5-enyl, dec-6-enyl, dec-7-enyl, dec-8-enyl, dec-9-enyl; undec-1-enyl, undec-2-enyl, undec-3-enyl, undec-4-enyl, undec-5-enyl, undec-6-enyl, undec-7-enyl, undec-8-enyl, undec-9-enyl, undec-10-enyl; dodec-1-enyl, dodec-2-enyl, dodec-3-enyl, dodec-4-enyl, dodec-5-enyl, dodec-6-enyl, dodec-7-enyl, dodec-8-enyl, dodec-9-enyl, dodec-10-enyl, dodec-11-enyl; buta-1,3-dienyl or penta-1,3-dienyl.

Alkynyl groups in the context of the present invention, unless defined differently, are linear, branched or cyclic hydrocarbyl groups containing at least one double unsaturation (triple bond). The definition $C_2$-$C_{12}$-alkynyl encompasses the widest range defined herein for an alkynyl group. Specifically, this definition encompasses, for example, the meanings of ethynyl(acetylenyl); prop-1-ynyl and prop-2-ynyl.

Cycloalkyl: monocyclic, saturated hydrocarbyl groups having 3 to 8 and preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

Aryl groups in the context of the present invention, unless defined differently, are aromatic hydrocarbyl groups which may have one, two or more heteroatoms selected from O, N, P and S. The definition $C_{6-18}$-aryl encompasses the widest range defined herein for an aryl group having 5 to 18 skeleton atoms, where the carbon atoms may be exchanged for heteroatoms. Specifically, this definition encompasses, for example, the meanings of phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Arylalkyl groups (aralkyl groups) in the context of the present invention, unless defined differently, are alkyl groups which are substituted by aryl groups, may have one $C_{1-8}$-alkylene chain and may have, in the aryl skeleton, one or more heteroatoms selected from O, N, P and S. The definition $C_{7-19}$-aralkyl group encompasses the widest range defined herein for an arylalkyl group having a total of 7 to 19 atoms in the skeleton and alkylene chain. Specifically, this definition encompasses, for example, the meanings of benzyl and phenylethyl.

Alkylaryl groups (alkaryl groups) in the context of the present invention, unless defined differently, are aryl groups which are substituted by alkyl groups, may have one $C_{1-8}$-alkylene chain and may have, in the aryl skeleton, one or more heteroatoms selected from O, N, P and S. The definition $C_{7-19}$-alkylaryl group encompasses the widest range defined herein for an alkylaryl group having a total of 7 to 19 atoms in the skeleton and alkylene chain. Specifically, this definition encompasses, for example, the meanings of tolyl or 2,3-, 2,4-, 2,5-, 2,6-, 3,4- or 3,5-dimethylphenyl.

The term intermediate used in the context of the present invention describes the substances which occur in the process according to the invention and are prepared for further chemical processing and are consumed or used therein in order to be converted to another substance. The intermediates can often be isolated and intermediately stored or are used without prior isolation in the subsequent reaction step. The term "intermediate" also encompasses the generally unstable and short-lived intermediates which occur transiently in multistage reactions (staged reactions) and to which local minima in the energy profile of the reaction can be assigned.

The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms.

Process Description

The process is illustrated in Scheme 1:

Scheme 1:

Step (A)

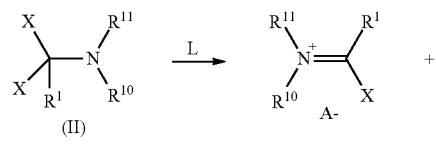

(II)

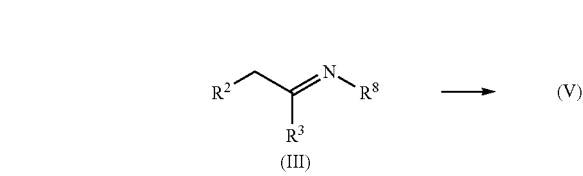

(III)

Step (B)

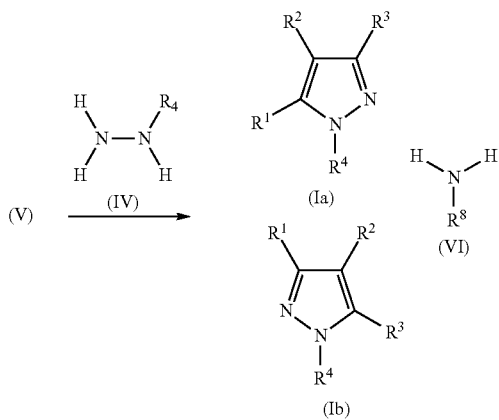

Step (A)

In step (A), α,α-dihaloamines of the formula (II) are first reacted, in the presence of a Lewis acid [L], with compounds of the formula (III).

Preferred compounds of the general formula (II) are 1,1,2,2-tetrafluoroethyl-N,N-dimethylamine (TFEDMA), 1,1,2,2-tetrafluoroethyl-N,N-diethylamine, 1,1,2-trifluoro-2-(trifluoromethyl)ethyl-N,N-dimethylamine, 1,1,2-trifluoro-2-(trifluoromethyl)ethyl-N,N-diethylamine (Ishikawa's reagent), 1,1,2-trifluoro-2-chloroethyl-N,N-dimethylamine and 1,1,2-trifluoro-2-chloroethyl-N,N-diethylamine (Yarovenko's reagent).

Compounds of the general formula (II) are used as iminoalkylating agents. Preference is given to 1,1,2,2-tetrafluoroethyl-N,N-dimethylamine (TFEDMA) and 1,1,2,2-tetrafluoroethyl-N,N-diethylamine, and particular preference to 1,1,2,2-tetrafluoroethyl-N,N-dimethylamine. α,α-Dihaloamines such as TFEDMA and Ishikawa's reagent are commercially available or can be prepared (cf. Yarovenko et al., Zh. Obshch. Khim. 1959, 29, 2159, Chem. Abstr. 1960, 54, 9724h or Petrov et al., J. Fluor. Chem. 109 (2011) 25-31).

Yagupolskil et al. (Zh. Organicheskoi Khim. (1978), 14(12), 2493-6) shows that the reaction of Yarovenko's reagent (FClCHCF$_2$NEt$_2$) with nitriles of the formula RCH$_2$CN (R=CN, CO$_2$Et) affords the derivatives of the formula (NC)RC=C(NEt$_2$)CHFCl in approx. 70% yield. Compounds of the formula (III) do not react with α,α-dihaloamines of the formula (II) under this condition.

Petrov et al. (J. of Fluorine Chem. (2011), 132(12), 1198-1206) shows that TFEDMA (HCF$_2$CF$_2$NMe$_2$) reacts with cyclic β-diketones to transfer a difluoroacetyl group.

In a preferred embodiment of the process according to the invention, the α,α-dihaloamine is first reacted with Lewis acid [L], for example BF$_3$, AlCl$_3$, SbCl$_5$, SbF$_5$, ZnCl$_2$, and then the mixture of the compound of the formula (III) is added in substance or dissolved in a suitable solvent (cf. WO 2008/022777).

α,α-Dihaloamines are reacted with Lewis acids (preparation of the iminium salts of the formula (V)) according to the teaching of WO 2008/022777. According to the invention, the reaction is effected at temperatures of −20° C. to +40° C., preferably at temperatures of −20° C. to +30° C., more preferably at −10 to 20° C. and under standard pressure. Due to the hydrolysis sensitivity of the α,α-dihaloamines, the reaction is conducted in anhydrous apparatuses under inert gas atmosphere.

The reaction time is not critical and may, according to the batch size and temperature, be selected within a range between a few minutes and several hours.

According to the invention, 1 mol of the Lewis acid [L] is reacted with equimolar amounts of the α,α-dihaloamine of the formula (II).

For the process according to the invention 1 to 2 mol, preferred 1 to 1.5 mol, most preferred 1 to 1.2 mol of the α,α-dihaloamine of the formula (II) is reacted with 1 mol compound of formula (III).

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane. Particular preference is given, for example, to THF, acetonitriles, ethers, toluene, xylene, chlorobenzene, n-hexane, cyclohexane or methylcyclohexane, and very particular preference, for example, to acetonitrile, THF, ether or dichloromethane.

The intermediates of the formula (V) formed can be used in the cyclization step without prior workup.

Especially the intermediates of the formula V-2 could be easily isolated from reaction mixture in pure form upon dilution with water. Isolated compounds of the formula V-2 are stable upon storage and react with hydrazine of the formula IV yielding the desired pyrazoles of the formula (I) in high and purity >95-96, so no further purification is needed.

Alternatively, the intermediates can be isolated by suitable workup steps, characterized and optionally further purified.

Compounds of formula (III) are partially new. They can be prepared from aldehydes or ketones (VII) according to the scheme shown below, see also Roeschenthaler et al, J. Fluorine. Chem. v. 125, n. 6, 1039-1049 and Tetrahedron, 69 (2013), 3878-3884.

Scheme 2:

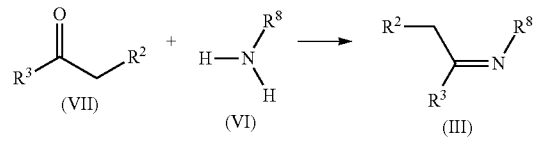

The reaction of compound (VII) and (VI) according to the invention is effected at temperatures of −40° C. to +120° C., preferably at temperatures of +20° C. to +100° C., more preferably at 20° C. to +60° C. and under standard pressure.

For the process according to the invention 0.9 to 2 mol, preferred 1 to 1.8 mol, most preferred 1 to 1.2 mol of the compound of the formula (VI) is reacted with 1 mol compound of the formula (VII).

In case R$^3$ is CF$_3$, CF$_2$H, CF$_2$Cl and R$^2$ is H it is preferable to use an excess of compound of the formula (VII), 1.02 to 2 mol, preferably 1.01 to 1.8 mol, most preferably 1.01 to 1.2 mol, of the compound of the formula (VII) for 1 mol compound of the formula (VI).

The reaction time is not critical and may, according to the batch size and temperature, be selected within a range between a few and many hours.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane, alcohols such as methanol, ethanol, isopropanol butanol, esters like ethyl- and propylacetate. Particular preference is given to ethylacetate, THF, acetonitriles, ethers, toluene, xylene, chlorobenzene, n-hexane, cyclohexane or methylcyclohexane, ethanol and very particular preference to ethylaacetate, toluene, acetonitrile, THF, ether, dichloromethane, ethanol. Most preferred is toluene.

Step (B)

According to the invention, 1 mol to 2 mol, preferably 1 to 1.5 mol of the hydrazine of the formula $NH_2$—$NHR^4$ for 1 mol of compound of formula (V) is used.

The cyclization in step (B) of the compound of formula (V) is effected at temperatures of −40° C. to +80° C., preferably at temperatures of +20° C. to +70° C., more preferably at +60° C. and under standard pressure.

The reaction time is not critical and may, according to the batch size, be selected within a relatively wide range.

Typically, the cyclization step (B) is effected without changing the solvent.

Typically the cyclization of compound of the formula (V) proceeds under acidic condition.

Preference is given to mineral acids, for example $H_2SO_4$, HCl, HF, HBr, HI, $H_3PO_4$ or organic acids, for example $CH_3COOH$, $CF_3COOH$, p-toluenesulphonic acid, methanesulphonic acid, trifluoromethanesulphonic acid.

According to the invention, 0.1 mol to 2 mol, preferably 0.1 to 1.5 mol of the acid for 1 mol of the compound of formula (V) is used.

Suitable solvents are, for example, aliphatic, alicyclic or aromatic hydrocarbons, for example petroleum ether, n-hexane, n-heptane, cyclohexane, methylcyclohexane, benzene, toluene, xylene or decalin, and halogenated hydrocarbons, for example chlorobenzene, dichlorobenzene, dichloromethane, chloroform, tetrachloromethane, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; alcohols such as methanol, ethanol, isopropanol or butanol, nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoramide; sulphoxides such as dimethyl sulphoxide or sulphones such as sulpholane, esters like ethyl-, isopropyl- and propylacetate. Particular preference is given, for example, to isopropylacetate, ethylacetate, acetonitrile, toluene, xylene, chlorobenzene, n-hexane, cyclohexane or methylcyclohexane, and very particular preference, for example, to ethylacetate, acetonitrile, THF, toluene, isopropylacetate or xylene. After the reaction has ended, for example, the solvents are removed and the product is isolated by filtration or distillation, or a solution of product is first washed with water, the organic phase is concentrated under reduced pressure.

The compounds of the formula (Ia/b) where $R^2$ is $COOR^4$ can then be converted to pyrazole acids of the formula (I) with $R^2$ being COOH.

Amine (VI) can be reused for the preparation of compound (III). Alternatively, it is trapped by washing the reaction mixture with acid.

The inventive compounds (Ia) and (Ib) are used for preparation of active fungicidal ingredients.

Example 1

N-(1,1-difluoropropan-2-ylidene)propan-2-amine, (III-1)

To the mixture of difluoracetone (94 g, 1 mol) in 500 ml methyltert.butylether (88 g, 1.5 mol) of isopropylamin was added at 10° C. After 1 h (70 g 0.5 mol) of $BF_3*Et_2O$ was added and the mixture was stirred additionally for 1 h. Organic solution was separated from bottom syrup and solvent was distilled off at atmospheric pressure. The remaining liquid was distilled in vacuum yielding 139 g ketimine with a of b.p. 70-72° C./400 mbar.

$^1H$ NMR (601 MHz, $CDCl_3$): δ: 5.83 (t, 1H), 3.74 (m, 1H), 1.92 (s, 3H), 1.15 (d, 6H) ppm.

$^{19}F$ (566 MHz, $CDCl_3$): δ: −121.4 (d, 2F) ppm.

Example 2

N-1,1-difluoropropan-2-ylidene-1-phenylmethanamine, (III-2)

To the mixture of difluoroacetone (94 g, 1 mol) in 500 ml dichloromethane, (107 g, 1 mol) of benzylamine was slowly added at 10° C. After 6 h at 20° C. $CH_2C_{12}$ was distilled off at reduced pressure and the remains liquid was distilled in vacuum, yielding 161 g ketimine with b.p. 80-82° C./1.3 mbar.

$^1H$ NMR (601 MHz, $CDCl_3$) δ: 7.36-7.26 (m, 5H), 5.94 (t, 1H), 4.55 (s, 2H), 2.03 (s, 3H) ppm.

$^{19}F$ (566 MHz, $CDCl_3$) δ: −−121.2 (dt, 2F) ppm.

Example 3

N-(1,1,1-trifluoropropan-2-ylidene)propan-2-amine, (III-3) (Preparation See Example 2), b.p. 80-82° C.

Example 4

N-1,1,1-trifluoropropan-2-ylidene-1-phenylmethanamin (III-4) (Preparation see Example 2) b.p. 90-91° C., 1.5 mbar Example 5

3,5-bis(difluoromethyl)pyrazole, (I-1)

300 ml of acetonitrile were placed in a double jacketed flask and cooled to 0° C. $AlCl_3$ 74.4 g (0.553 mol) was added portionwise at this temperature under intensive stirring to form yellow suspension. To this suspension a solution of TFEDMA 80 g (0.553 mol) in 350 ml acetonitrile was added at 10° C. The reaction mixture was stirred for 1 h at room temperature and solution of (53 g, 0.395 mol) of N-1,1(-difluoropropan-2-ylidene) propan-2-amine was added within 1 h at 40° C. and the mixture was stirred at this temperature for 12 h. 100 ml HCl (as 5% water solution) and 29 g hydrazinhydrate were added slowly to the reaction solution to keep the temperature under 40° C. and the mixture was stirred for 5 h at 60° C. forming two phases. The upper organic layer was separated, diluted with 500 ml methyltertbutylether, washed two times with water, dried over $MgSO_4$ and concentrated in vacuum to give an oily product. Vacuum distillation at 92-95° C./1 mbar gave 56.4 g (85%) of pure 3,5-bis(difluoromethyl)-1H-pyrazole b) as a white solid with a of m.p. 70-71° C.

$^1$H NMR (601 MHz, $CDCl_3$) δ 11.93 (br, 1H), 6.88 (t, 2H, J=54.8 Hz), 6.79 (s, 1H) ppm.
$^{13}$C NMR (151 MHz, CDCN) δ 103.4 (p); 111.1 (t); 143.6 (br) ppm.
$^{19}$F NMR (566 Mhz), δ: −112.2 (d, br) ppm.

Example 6

3,5-bis(difluoromethyl)pyrazole, (I-1)

$BF_3$ (247 g 0.553 mol) as 15% Solution in $CH_3CN_3$ was placed in the flask and a solution of TFEDMA 80 g (0.553 mol) in 350 ml acetonitrile was added at 10° C. portionwise at this temperature under intensive stirring. The reaction mixture was stirred for 1 h at room temperature and solution of (53 g, 0.395 mol) of N-1,1(-difluoropropan-2-ylidene) propan-2-amine was added within 1 h at 40° C. and the mixture was stirred at this temperature for 12 h. 20 ml HCl and 29 g hydrazinhydrate were added slowly to the reaction mixture to keep the temperature under 40° C. and the mixture was stirred for 5 h at 60° C. Volatiles were removed in vacuum, 300 ml methyltertbutylether was added to the residues and organic solution was washed two times with water, dried over $MgSO_4$ and concentrated in vacuum to give an oily product. Vacuum distillation at 92-95° C./1 mbar gave 58 g (87%) of pure 3,5-bis(difluoromethyl)-1H-pyrazole as a white solid with m.p. 70-71° C. $^1$H NMR (601 MHz, $CDCl_3$) δ 11.93 (br, 1H), 6.88 (t, 2H, J=54.8 Hz), 6.79 (s, 1H).

EXAMPLE 3-(difluoromethyl)-5-(trifluoromethyl)-1H-pyrazole, (I-2)

30 ml of acetonitrile were placed in a double jacketed flask and cooled to 0° C. $BF_3.Et_2O$ 4.8 g (0.055 mol) was added portionwise at this temperature under intensive stirring to form yellow solution. A solution of TFEDMA 8 g (0.0 55 mol) in 35 ml acetonitrile was added at 10° C. and reaction mixture was stirred for 1 h at room temperature. A solution of (5, 3 g, 0.0395 mol) of N-(1,1,1-trifluoropropan-2-ylidene]propan-2-amine was added within 1 h at 40° C. and the mixture was stirred at 40° C. for 12 h. 15 ml HCl (as 5% water solution) and 2.9 g hydrazinhydrate was added slowly to the reaction solution to keep the temperature under 40° C. and the reaction mixture was stirred for 5 h at 60° C. Water (10 mL) was added and the solution was extracted with methyltertbutylether (3×20 mL). The combined organic extracts were washed with brine (15 mL), dried over $Na_2SO_4$ and evaporated under reduced pressure. The crude material was purified by column chromatography on silica gel with pentane/diethyl ether (100:0 to 60:40) as eluent to afford the pure title compound (6.2 g, 85%) as a pale yellow solid.

$^1$H NMR (400 MHz, $CDCl_3$) δ 12.6 (br, 1H), 6.81 (s, 1H), 6.76 (t, 1H, J=54.5 Hz); $^{13}$C (101 MHz, $CDCl_3$) δ 140.7, 128.8, 120.3 (q, $J_{C-F}$=266 Hz), 108.5 (t, $J_{C-F}$=237 Hz), 103.8; $^{19}$F (376 MHz, $CDCl_3$) δ −61.7 (s, 3F), −112.9 (d, 2F, J=54.7 Hz); HRMS (ESI) calculated for $C_5H_4F_5N_2$ $[M+H]^+$ 187.029. found 187.029.

Example 8

(3 E/Z)-4-(benzylamino)-1,1,5,5-tetrafluoro-N,N-dimethylpent-3-en-2-iminium-tetrafluoroborate, (V-1-1)

$BF_3$ (2.47 g 0.0553 mol) as 15% solution in $CH_3CN_3$ was placed in the flask and a solution of TFEDMA 8 g (0.0553 mol) in 35 ml acetonitrile was added at 10° C. portionwise at this temperature under intensive stirring. The reaction mixture was stirred for 1 h at room temperature and solution of (10.1 g, 0.0553 mol) of N-1,1-difluoropropan-2-ylidene-1-phenylmethanamine was added within 1 h at 40° C. and the mixture was stirred at this temperature for 12 h. The solvent was removed in vacuum 2 mbar. The oily product was analyzed via NMR spectroscopy showing pure compound.

$^{13}$C-NMR-Spectra

The $^{13}$C NMR data were taken from HSQC and HMBC spectra. The data are referenced to $CD_3CN$ (1.3 ppm).
$^{13}$C NMR (151 MHz, $CD_3CN$) δ 164.8 (s, t), 159.5 (st); 135.1 (s); 129.6 (d), 129.0 (d), 128.4 (d); 110.6 (dt), 109.6 (dt), 86.7 (d); 49.2 (t); 46.1 (q, br); 43.7 (q, br) ppm.
$^1$H NMR (601 MHz, $CD_3CN$) δ: 8.26 (br.s. 1H)), 7.42 (m, 2H), 7.37 (m, 3H), 6.73 (t, 1H), 6.64 (t, 1H), 5.09 (s, br, 1H), 4.58 (s, br, 2H), 3.33 (s, br 6H) ppm.

An interaction of (3 E/Z)-4-(benzylamino)-1,1,5,5-tetrafluoro-N,N-dimethylpent-3-en-2-iminium tetrafluoroborate with $N_2H_4$ and HCl in Ethanol according to the conditions in example 5 gave pure 3,5-bis(difluoromethyl)pyrazole in 89% yield.

Example 9

(4E- and 4Z)-benzylimino-1,1,5,5-tetrafluoro-pentan-2-one (V-2-1)

To a solution of 318 g of $BF_3$ (as 15.2% w.w. solution in $CH_3CN$) 107 g of Tetrafluoroethyldimethylamin was added at 0 to 5° C. within 40 minutes. The pale yellow solution was stirred additionally for 1 h at 0° C. and the mixture was heated up to 40° C. within 1 h. 122.6 g of N-benzyl-1,1-difluoro-propan-2-imine was added at 40° C. so fast to maintain the temperature in the reactor between 40-45° C. (addition time 45 min). The reaction mixture was stirred additionally for 2 h at 40° C. to give clear pale/yellow solution. Under stirring 200 ml water were added to this solution at 0° C. and after 10-15 min a white precipitates starts to form. The slurry was stirred for 3-4 h at 0° C. and the precipitate was filtered off, washed with 100 ml of water and dried at 40° C. to give 152.2 g (yield 89%) of the product as a white solid with a melting point of 86-87° C.

Mixture of E/Z-isomers in ratio 25:75.NMR $^{19}$F (566 MHz, $CD_3CN$, $CFCl_3$): E-isomer: −123.2 (d), −125.2 (d) ppm.
Z-isomer: −120.8 (d), −125.9 (d)

¹H NMR (601 MHz, CD3CN): E-isomer 25%: 4.43, (d, 2H); 5.42, (s, 1H); 5.77, (t, 1H); 7.32 (t, 1H), 7.33, (m, 2H); 7.42-7.32, m, (5H); 10.67 (s, br, 1H) ppm.

Z-isomer 75%: 4.65, (d, 2H); 5.69, (s, 1H); 5.92, (t, 1H); 6.55 (t, 1H), 5.92 (t, 1H), 7.34, (m 2H), 7.42-7.32, (m, 5H); 10.67 (s, br, 1H) ppm.

Example 10

(4E- and 4Z)-isopropylimino-1,1,5,5-tetrafluoro-pentan-2-one (V-2-2)

To a solution of 24.5 of $BF_3$ (as 15.2% w.w. solution in $CH_3CN$) 8.2 g of Tetrafluoroethyldimethylamin was added at 0 to 5° C. within 40 minutes. The pale yellow solution was stirred additionally for 1 h at 0° C. and the mixture was heated up to 40° C. within 1 h. 6.75 g of N-isopropyl-1,1-difluoro-propan-2-imine was added at 40° C. so fast to maintain the temperature in reactor between 40-45° C. (addition time 45 min). The reaction mixture was stirred additionally for 2 h at 40° C. to give clear pale/yellow solution. Under stirring 50 ml water were added to this solution at 0° C. and two-phase mixture was stirred for 1 h at 0° C. and the product extracted with ethylacetate, Organic extract was washed with 100 ml of water and dried over $MgSO_4$ to give 9.5 g (yield 89%) of the oil as a mixture of Z/E-isomers in ratio 83:17.

NMR ¹⁹F (566 MHz, $CD_3CN$): Z-isomer: −120.5 (d), −125.7 (d) ppm.

E-isomer: −123.1 (d), −125.0 (d) ppm.

¹H NMR (601 MHz, $CD_3CN$) E/Z-isomers: 1.23, 1.27 (D, 6H); 3.72, 3.97 (M, 1H); 5.43, 5.57 (S, 1H); 5.85, 7.33, 5.90, 6.53 (T, 1H); 10.52 (S, br, 1H) ppm.

m/z: 213.

Example 11

3,5-bis(difluoromethyl)pyrazole (I-1)

2.4 g of hydrazine-hydrate were added dropwise to the suspension of 10.4 g (4E and 4Z)-benzylimino-1,1,5,5-tetrafluoro-pentan-2-one in 60 ml ethylacetate. The mixture was stirred for 1 h at room temperature and then 15.6 g of 30% $H_2SO_4$ were added dropwise to reaction mixture. The slurry was stirred for 2 h at 20° C., precipitate was filtered off and organic phase washed with water. The solvent was removed in vacuum to give 6.5 g of the product with a melting point of 73-74° C.

¹H NMR (601 MHz, $CDCl_3$) δ 12.5 (br, 1H), 6.77 (t, 2H, J 54.8 Hz), 6.74 (s, 1H).

Example 12

N-methyl-3,5-bis(difluoromethyl)pyrazole (I-3)

To a suspension of 2.6 g of (4E and 4Z)-benzylimino-1,1,5,5-tetrafluoro-pentan-2-one in 20 ml of ethanol 0.5 g N-methylhydrazine was added at 20° C. The mixture was stirred for 1 h and then acidified by adding of 3.6 g of 30% $H_2SO_4$. After 1 h the mixture was evaporated in vacuum and product extracted with methyltert.butylether. Organic phase was washed with water and concentrated in vacuum to give 1.7 g (yield 94%) of oily product.

¹H NMR (601 MHz, $CD_3CN$) δ 3.95 (s, 3H), 6.77 (t, 1H, ²J=54.7 Hz); 6.78 (s, 1H); 6.95 (t, 1H, ²J=53.4 Hz) ppm.

¹⁹F NMR (566 MHz, $CD_3CN$, $CFCl_3$) δ: −112.8 (d); 115.4 (d) ppm.

m/z: 182.

Example 13

Ethyl [3,5-bis(difluoromethyl)-1H-pyrazol-1-yl]acetate (I-4)

To a suspension of 0.7 g of (4E and 4Z)-benzylimino-1,1,5,5-tetrafluoro-pentan-2-one in 20 ml of ethanol 0.45 g of ethyl hydrazinoacetate hydrochloride was added at 20° C. The mixture was stirred for 10 h at 40° C. and then acidified by adding of 0.95 g of 30% $H_2SO_4$. After 1 h the mixture was evaporated in vacuum and product extracted with methyltert.butylether. Organic phase was washed with water and concentrated in vacuum to give 1.7 g (yield 94%) of oily product.

¹H NMR (601 MHz, $CD_3CN$) δ: 1.24 (t, 3H), 4.20 (q, 2H), 5.07 (s, 2H) 6.79 (t, 1H, J=54.7 Hz); 6.86 (s, 1H); 6.94 (t, 1H, J=53.5 Hz) ppm.

¹⁹F NMR (566 MHz, $CD_3CN$) δ: −112.7 (d); −115.4 (d) ppm.

m/z: 254

Example 14 (to Demonstrate the Use of Pyrazoles for the Preparation of Fungicides)

2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate

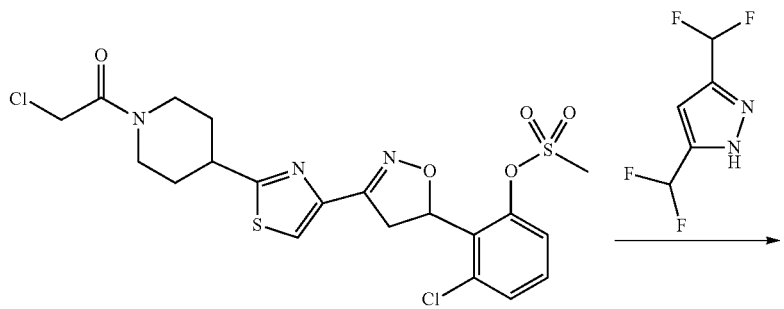

-continued

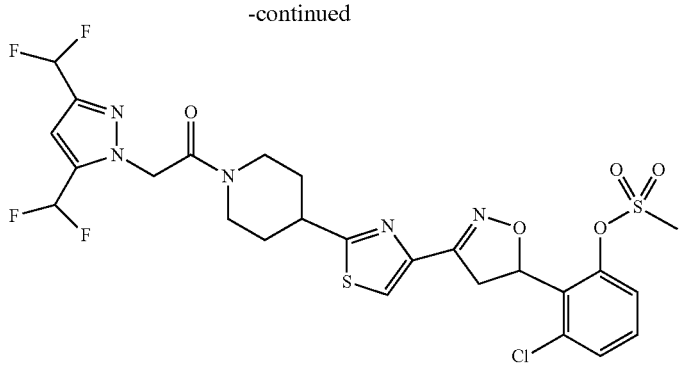

16 g (0.03 mol) of 3-chloro-2-(3-{2-[1-(chloroacetyl) piperidin-4-yl]-1,3-thiazol-4-yl}-4,5-dihydro-1,2-oxazol-5-yl)phenyl methanesulfonate, 5.7 g (0.033 mol) 3,5-bis(difluoromethyl)-1H-pyrazole, 4.9 g (0.046 mol) sodium carbonate and 1.5 g (0.005 mol) tetrabutylammonium bromide are suspended in 100 ml acetonitrile. The mixture is heated up to 70° C. and stirred for 3.5 hours. At 40° C. most of the solvent is distilled off in vacuum and replaced by 100 ml of toluene. The mixture is cooled to 20° C., stirred for 1 hour, seeded and then cooled to 5° C. and stirred for 1 hour. A mixture of 20 ml of water and 6 ml 20% HCl is added and stirred for 30 minutes. The solid is filtered off, washed with toluene and water and dried at 45° C. in vacuum.

18 g of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate with a purity of 94% is received (yield: 84%).

The invention claimed is:
1. Process for preparing a 3,5-bis(haloalkyl)pyrazole of formula (Ia) and (Ib)

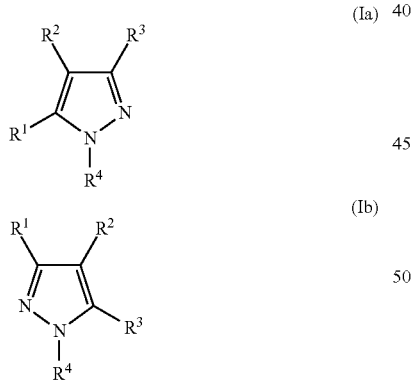

in which
R$^1$ and R$^3$ are each independently selected from C$_1$-C$_6$-haloalkyl;
R$^2$ is selected from H, halogen, COOH, (C=O)OR$^5$, CN and (C=O)NR$^6$R$^7$;
R$^4$ is selected from H, C$_1$-C$_8$-alkyl, CH$_2$COOC$_1$-C$_8$-alkyl, aryl, pyridyl;
R$^5$ is selected from C$_1$-C$_{12}$-alkyl, C$_3$-C$_8$-cycloalkyl, C$_6$-C$_{18}$-aryl, C$_7$-C$_{19}$-arylalkyl and C$_7$-C$_{19}$-alkylaryl;
R$^6$ and R$^7$ are each independently selected from C$_1$-C$_{12}$-alkyl, C$_3$-C$_8$-cycloalkyl, C$_6$-C$_{18}$-aryl, C$_7$-C$_{19}$-arylalkyl and C$_7$-C$_{19}$-alkylaryl or where R$^6$ and R$^7$ together with the nitrogen atom to which they are bonded may form a four-, five- or six-membered ring
wherein in one or more (A), α,α-dihaloamines of formula (II),

in which
R$^1$ is as defined above;
X is independently selected from F, Cl or Br,
R$^{10}$ and R$^{11}$ are each independently selected from C$_1$-C$_{12}$-alkyl, C$_3$-C$_8$-cycloalkyl, C$_6$-C$_{18}$-aryl, C$_7$-C$_{19}$-arylalkyl and C$_7$-C$_{19}$-alkylaryl or where
R$^{10}$ and R$^{11}$ together with the nitrogen atom to which they are bonded may form a five- or six-membered ring;
are reacted with one or more compounds of formula (III),

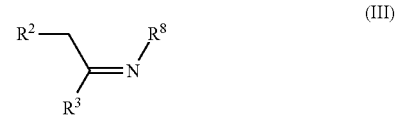

in which
R$^8$ is selected from C$_1$-C$_{12}$-alkyl, C$_3$-C$_8$-cycloalkyl, C$_6$-C$_{18}$-aryl, C$_7$-C$_{19}$-arylalkyl and C$_7$-C$_{19}$-alkylaryl, OR$^9$;
R$^9$ is selected from C$_1$-C$_{12}$-alkyl, C$_3$-C$_8$-cycloalkyl, C$_6$-C$_{18}$-aryl, C$_7$-C$_{19}$-arylalkyl, C$_7$-C$_{19}$-alkylaryl;
R$^2$ and R$^3$ are as defined above;
to form the compound of formula (V): (V-1), (V-2), (V-3), (V-4) and (V-5)

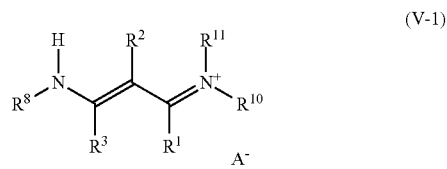

-continued

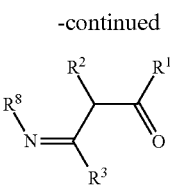
(V-2)

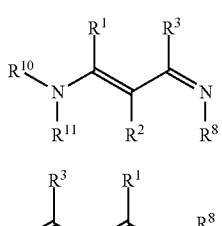
(V-3)

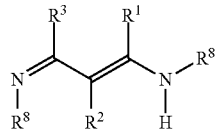
(V-4)

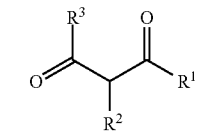
(V-5)

A⁻ is $BF_4^-$, $AlCl_3F^-$, $AlF_2Cl_2^-$, $AlF_3Cl^-$ or $ZnCl_2F^-$
$R^1, R^2, R^3, R^5, R^6, R^7, R^8, R^9, R^{10}, R^{11}$ are as defined above and wherein in (B) in the presence of hydrazine $H_2N$—$NHR^4$ (IV)—with $R^4$ being as defined above, —a cyclization of (V) takes place to form (Ia/Ib).

2. Process according to claim 1, wherein
$R^1$ and $R^3$ are each independently selected from difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-difluoroethyl, 2,2-dichloro-2-fluoroethyl, 2,2,2-trichloroethyl, tetrafluoroethyl ($CF_3CFH$), pentafluoroethyl and 1,1,1-trifluoroprop-2-yl;
$R^2$ is selected from H, F, Cl, Br, $COOCH_3$, $COOC_2H_5$, $COOC_3H_7$, CN and $CON(CH_3)_2$, $CON(C_2H_5)_2$;
$R^4$ is selected from H, $C_1$-$C_8$-alkyl, $CH_2COOC_1$-$C_8$-alkyl, phenyl, pyridyl;
$R^8$ are each independently selected from methyl, ethyl, n-, iso-propyl, n-, iso-, sec- and t-butyl, cyclopropyl, cyclobutyl, cyclopentyl, cyclohexyl, phenyl, benzyl, phenylethyl, $C_7$-$C_{19}$-alkylaryl, tolyl, 2,3-, 2,4-, 2,5-, 2,6-, 3,4- or 3,5-dimethylphenyl;
X is independently selected from F or Cl;
$R^{10}$ and $R^{11}$ are each independently selected from $C_1$-$C_{12}$-alkyl, $C_3$-$C_8$-cycloalkyl, $C_7$-$C_{19}$-arylalkyl or
$R^{10}$ and $R^{11}$ together with the nitrogen atom to which they are bonded may form a five-membered ring.

3. Process according to claim 1, wherein
$R^1$ and $R^3$ are each independently selected from trifluoromethyl, difluoromethyl, difluorochloromethyl, pentafluoroethyl;
$R^2$ is selected from H, Cl, CN, $COOC_2H_5$;
$R^4$ is selected from H, methyl, ethyl, n-, isopropyl, n-, iso-, sec- and t-butyl, n-pentyl, n-hexyl, 1,3-dimethylbutyl, 3,3-dimethylbutyl, phenyl, $CH_2COOCH_3$, $CH_2COOCH_2CH_3$;
$R^8$ is selected from methyl, ethyl, n-, iso-propyl, n-, iso-, sec- and t-butyl, cyclopropyl, cyclobutyl, cyclopentyl, cyclohexyl, benzyl, $C_7$-$C_{19}$-alkylaryl;
X is independently selected from F or Cl;

$R^{10}$ and $R^{11}$ are each independently selected from $C_1$-$C_{12}$-alkyl, $C_3$-$C_8$-cycloalkyl.

4. Process according to claim 1, wherein,
$R^1$ and $R^3$ are each independently selected from $CF_2H$ and $CF_3$;
$R^2$ is selected from H or $COOC_2H_5$;
$R^4$ is selected form H, methyl, ethyl, $CH_2COOCH_3$, $CH_2COOCH_2CH_3$, phenyl;
$R^8$ is selected from ethyl, n-, iso-propyl, n-, cyclopentyl, cyclohexyl, benzyl;
X is F;
$R^{10}$ and $R^{11}$ are each independently selected from $C_1$-$C_{12}$-alkyl.

5. Process according to claim 1, wherein,
$R^1$ and $R^3$ are $CF_2H$;
$R^2$ is H;
$R^4$ is selected from H, methyl, $CH_2COOCH_2CH_3$, phenyl;
$R^8$ is selected from iso-propyl and benzyl;
X is F;
$R^{10}$ and $R^{11}$ are each independently selected from methyl and ethyl.

6. Compound of formula (V-1)

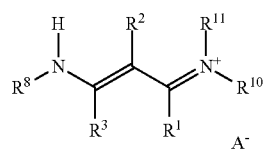
(V-1)

in which
$R^1$ and $R^3$ are $HCF_2$;
$R^2$ is H;
$R^8$ is selected from $C_1$-$C_{12}$-alkyl, $C_3$-$C_8$-cycloalkyl and benzyl;
$R^{10}$ and $R^{11}$ are each independently selected from $C_1$-$C_5$ alkyl;
A is $BF_4^-$.

7. Compound of formula (V-2)

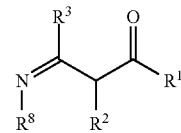
(V-2)

in which
$R^1$ and $R^3$ are $HCF_2$;
$R^2$ is H;
$R^8$ is selected from $C_1$-$C_{12}$-alkyl, $C_3$-$C_8$-cycloalkyl and benzyl.

8. Compound of formula (V-3)

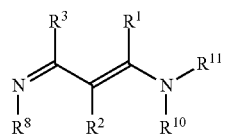
(V-3)

in which
$R^1$ and $R^3$ are $HCF_2$;

$R^2$ is H;
$R^8$ is selected from $C_{1-12}$-alkyl, $C_{3-8}$-cycloalkyl and benzyl;
$R^{10}$ and $R^{11}$ are each independently selected from $C_{1-5}$ alkyl.
9. Compound of formula (V-4)
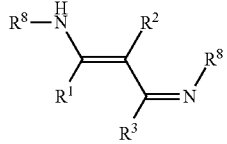
(V-4)
in which
$R^1$ and $R^3$ are $HCF_2$;
$R^2$ is H;
$R^8$ is selected from $C_{1-12}$-alkyl, $C_{3-8}$-cycloalkyl and benzyl.
* * * * *